United States Patent
Bistram

(10) Patent No.: US 7,875,085 B2
(45) Date of Patent: Jan. 25, 2011

(54) COLOR ENHANCING SHAMPOO COMPOSITION

(75) Inventor: Vera Bistram, Einhausen (DE)

(73) Assignee: KPSS-KAO Professional Salon Serivces GmbH, Darmstadt (DE)

( * ) Notice: Subject to any disclaimer, the term of this patent is extended or adjusted under 35 U.S.C. 154(b) by 81 days.

(21) Appl. No.: 12/174,433

(22) Filed: Jul. 16, 2008

(65) Prior Publication Data

US 2009/0178210 A1 Jul. 16, 2009

(30) Foreign Application Priority Data

Jul. 26, 2007 (EP) .................................. 07014675

(51) Int. Cl.
*C09B 67/02* (2006.01)
*A61K 8/00* (2006.01)

(52) U.S. Cl. .................. 8/525; 8/552; 8/554; 8/637.1; 424/70.1

(58) Field of Classification Search .............. 8/525, 8/552, 554, 637.1; 424/70.1
See application file for complete search history.

(56) References Cited

U.S. PATENT DOCUMENTS

2003/0069148 A1 * 4/2003 Booker et al. ............... 510/130
2003/0086897 A1 5/2003 Ohta et al.

FOREIGN PATENT DOCUMENTS

EP 1504749 A 2/2005
EP 1504749 A1 * 9/2005

OTHER PUBLICATIONS

STIC Search Report dated Dec. 4, 2009.*

* cited by examiner

*Primary Examiner*—Eisa B Elhilo
(74) *Attorney, Agent, or Firm*—Norris McLaughlin & Marcus, PA

(57) ABSTRACT

A coloring enhancing shampoo composition for hair comprising at least one cleaning and lathering surfactant selected from anionic, nonionic and amphoteric surfactants and present at a concentration of 5 to 50% by weight, calculated to total composition; at least one oil soluble dye; at least one polypropylene glycol compound having a formula as disclosed in the claims and the disclosure and optionally at least one silicone compound having at least one quaternary ammonium group.

16 Claims, No Drawings

COLOR ENHANCING SHAMPOO COMPOSITION

The present invention concerns a shampoo composition with color enhancing effect and showing optimum hair conditioning properties, especially shine, softness and good manageability.

Color enhancing and cleansing compositions have been known for many years and have proven to be very successful on the market.

Such shampoo compositions customarily comprise hair coloring direct dyestuffs together with the at least one surface-active substance, in particular an anionic surfactant, and a hair-conditioning polymer, preferably of the cationic type.

Although these products are proven as such to be satisfying consumer needs, it is still desirable to improve their efficiency especially in terms of hair shine, softness and manageability together with good colour enhancing ability, and certainly with other hair conditioning properties in particular with regard to volume and body, and combability.

Thus, the object of the present invention is providing a cleansing composition showing excellent colour enhancing and cleansing abilities together with excellent shine enhancing effect, improving excellently manageability and softness of hair, at the same time having optimum conditioning effects on hair, which satisfies consumer expectations in terms of combability, volume and body, and nice feeling on touching hair.

It has surprisingly been found out that a composition comprising at least one cleansing and lathering surfactant, at least one oil soluble dye and at least one polypropylene glycol compound according to the formula

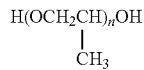

wherein n is a number in the range of 2 to 50, and at least one cationic surfactant of the following general formula

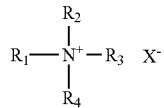

wherein $R_1$ is an saturated or unsaturated alkyl chain with 12 to 22 C atoms, or

where $R_5$ is saturated or unsaturated, alkyl chain with 7-21 C atoms and n has value of 1-4, or

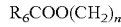

where $R_6$ is saturated or unsaturated, branched or non-branched alkyl chain with 7-21 C atoms and n has value of 1-4, and R2, R3 and R4 are same or different and independent from each other an alkyl group with 1 to 4 C atoms, and X is an anion such as chloride, bromide, methosulfate and/or at least one silicone compound with at least one quaternary ammonium group, cleanses and enhances colour and shine of hair.

Further object of the present invention is method of cleansing and colour enhancing wherein a composition as disclosed in the above paragraph is applied onto wet hair and foamed by massaging and rinsed of after a short processing time with water.

Further object of the present invention is the use of the composition disclosed in the above paragraph for cleansing and colour enhancing hair.

Further object of the present invention is method of producing cleansing and colour enhancing composition wherein oil soluble dye is dissolve in at least one polypropylene glycol and mixed with at least one cationic surfactant and/or silicone compound with at least one quaternary ammonium group subsequently added to the surfactant/water mixture which is furthermore added the remaining ingredients in the formulation.

With the term oil soluble it is meant that the dyestuff is soluble in the selected polypropylene glycol at the concentrations used in the formulations at room temperature or at temperatures where the composition is produced. Such temperatures may vary from room temperature to approximately 80° C.

Cleansing and colour enhancing compositions of the present invention comprise at least oil soluble dye. In principal any oil soluble dye is suitable for the purpose of the present invention. Non-limiting examples to suitable ones are with their colour index numbers CI 12100, CI 12140, CI 12700, CI 12740 CI 26100, CI 26105, CI 45396, CI 45410, CI 45425, CI 47000, CI 60725, CI 60724, CI 61520 and CI 61565.

Concentration of oil soluble dyes in the compositions of the present invention varies in the range of 0.001 to 1%, preferably 0.005 to 0.75, more preferably 0.01 to 0.5 and most preferably 0.05 to 0.25% by weight calculated to total composition.

Cleansing and colour enhancing composition of the present invention comprise at least one polypropylene glycol according to the following general formula

wherein n is a number between 2 and 50 preferably 2 and 30 more preferably 2 and 20.

Non-limiting examples are dipropylene glycol, PPG-3, PPG-9, PPG-12, PPG 15, PPG-16, PPG 20. Most preferred is dipropyleneglycol.

Concentration of the polypropylene glycol in the composition of the present invention varies between 0.1 and 10%, preferably 0.25 and 7.5% and more preferably 0.5 and 5%, and most preferably 0.75 to 3% by weight, calculated to total composition.

Compositions of the present invention comprise at least one mono alkyl quaternary ammonium surfactant with the given general formula above and/or a silicone compound with at least one quaternary ammonium group.

Non-limiting examples to mono alkyl quaternary ammonium surfactant are cetrimonium chloride, steartrimonium chloride, behentrimonium chloride, cocotrimonium methosulfate, cocotrimonium chloride, cocamidoproplyethyldimonium methosulfate, cocamidopropyltrimonium chloride and stearamidopropylethyldimonium methosulfate. Preferred are cetrimonium chloride, steartrimonium chloride and behentrimonium chloride. Most preferred is cetrimonium chloride.

Concentration of mono alkyl quaternary ammonium surfactant is in the range of 0.1 to 3%, preferably 0.2 to 2% more preferably 0.25 to 1.5% and most preferably 0.3 to 1% by weight calculated to total composition.

Silicone compounds comprising at least one quaternary ammonium group are comprised in the same concentration ranges as given for mono alkyl quaternary ammonium compounds.

As a rule any silicone compound carrying at least one quaternary ammonium group is suitable for the purpose of the present invention. Preferably the silicone compound comprises two quaternary ammonium groups.

Suitable examples are those known with the CTFA name silicone Quaternium-1 to 21 and Quaternium 80. The former ones include single quaternary ammonium group and the latter two quaternary ammonium groups.

Most preferred silicone compound with quaternary ammonium group is Quaternium-80 available from Degussa under the trade name Abil Quat.

Cleansing and colour enhancing compositions of the present invention comprise at least one cleansing and lathering surfactant. Cleansing colour enhancing compositions of the present invention comprise at least one surfactant selected from anionic, non-ionic and/or amphoteric or zwitterionic surfactants at a concentration range of 5 to 50%, preferably 5 to 40% and more preferably 5 to 30%, and most preferably 5 to 25% by weight, calculated to the total composition. In a preferred embodiment of the present invention, compositions comprise at least one non-ionic surfactant.

Especially suited and preferred nonionic surfactants are alkyl polyglucosides of the general formula

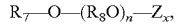

$R_7$—O—$(R_8O)_n$—$Z_x$, wherein $R_7$ is an alkyl group with 8 to 18 carbon atoms, $R_8$ is an ethylene or propylene group, Z is a saccharide group with 5 to 6 carbon atoms, n is a number from 0 to 10 and x is a number between 1 and 5.

These alkyl polyglucosides have recently become known in particular as excellent skin-compatible, foam improving agents in liquid detergents and body cleansing compositions, and are present in an amount from about 2% to 15%, in particular from 5% to 10% by weight, calculated to the total composition.

Further nonionic surfactant components are, for example, long-chain fatty acid mono- and dialkanolamides, such as coco fatty acid monoethanolamide and myristic fatty acid monoethanolamide, which can also be used as foam enhancers, preferably in amounts from about 1% to about 5% by weight.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "PluronicsR", as well as fatty alcohol ethoxylates.

Further suitable nonionic surfactants are aminoxides. Such aminoxides are state of the art, for example C12-C18-alkyl dimethyl aminoxides such as lauryl dimethyl aminoxide, C12-C18-alkyl amidopropyl or -ethyl aminoxides, C12-C18-alkyl di(hydroxyethyl) or (hydroxypropyl) aminoxides, or also aminoxides with ethyleneoxide and/or propyleneoxide groups in the alkyl chain. Such aminoxides are on the market, for example, under the trade names "Ammonyx®", "Aromox®" or "Genaminox®".

Further nonionic surfactants useful in the compositions according to invention are C10-C22-fatty alcohol ethoxylates at a concentration of 0.5 to 5%, preferably 0.5 to 3% by weight, calculated to total composition. Especially suited are C10-C22-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

Further, according to the preferred embodiment of the present invention compositions comprise at least one amphoteric surfactant.

In an embodiment of the present invention cleansing colouring enhancing composition of the present invention, comprises at least one nonionic surfactant and at least one amphoteric surfactant.

Amphoteric or zwitterionic surfactants are contained in the cleansing composition of the present invention in an amount from about 1% to about 10%, preferably from about 2% to about 5%, by weight, calculated to the total composition. It has especially been found out that addition of zwitterionic or amphoteric surfactants enhances foam feeling in terms of creaminess, foam volume and as well as skin compatibility is improved. For achieving milder formulations nonionic surfactant is mixed with amphoteric surfactant in a weight ratio range of 5:1 to 1:1, preferably 3:1 to 1:1.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

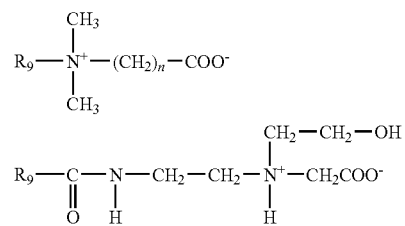

wherein $R_9$ is a $C_8$-$C_{18}$-alkyl group and n is 1 to 3; sulfobetaines of the structure

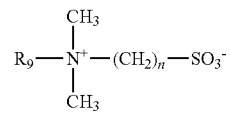

wherein $R_9$ and n are same as above;

and amidoalkyl betaines of the structure

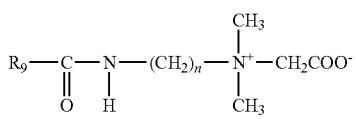

wherein R9 and n are same as above.

Anionic surfactants may be contained in the compositions of the present invention. It should be noted that anionic sulfate surfactants such as alkyle ether sulfate or alkyl sulfates are less preferred and therefore their concentration should not exceed approximately 2% by weight in the cleansing compositions. Other than sulfate types, carboxylate type of anionic surfactants are preferred in the cleansing compositions at a concentration of 2 to about 20%, preferably 5 to 20% and more preferably 5-15%, and most preferably 5 to 10% by weight, calculated to the total composition.

Less preferred are these are anionic surfactants of the sulfate, sulfonate and alkyl phosphate type, especially, of course, those customarily used in shampoo compositions, for example, the known C10-C18-alkyl sulfates, and in particular the respective ether sulfates, for example, C12-C14-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates constituting mild, skin-compatible detergents.

Further less preferred anionic surfactants within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable and preferred surfactants of the carboxylate type are alkyl polyether carboxylic acids and the salts thereof of the formula

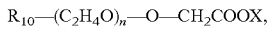

wherein $R_{10}$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

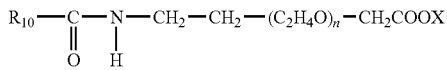

wherein $R_{10}$ and X have the above meanings, and n is in particular a number from 1 to 10, preferably 2.5 to 5.

Such products have been known for some time and are on the market, for example, under the trade name "AKYPO®" and "AKYPO-SOFT®".

It is also possible to use mixtures of several anionic surfactants, for example an ether sulfate and a polyether carboxylic acid or alkyl amidoether carboxylic acid.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

According to the invention, colour enhancing cleansing composition can further comprise at least one additional direct acting hair dye. Suitable dyes are anionic, cationic and nonionic nitro dyes.

In the preferred form compositions of the present invention comprise at least one cationic direct dye. Suitable cationic dyestuffs are in principal those available on the market for hair colouring applications. Some examples to those are:

Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12, Basic Red 51, Basic Red 22, Basic Red 76, Basic Violet 1, Basic Violet 2, Basic Violet 3, Basic Violet 10, Basic Violet 14, Basic Yellow 57 and Basic Yellow 87. For this purpose, special reference is made to the PCT application WO 95/15144 of Ciba-Geigy AG. All of the cationic dyes disclosed in the referred publication are suitable for the purpose of the present invention.

Anionic dyes may as well be used alone or in combination with cationic direct dyes. The suitable ones are: Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. It should be noted that colouring effect of those anionic dyes are much lower compared to the oil soluble ones and cationic dyes, and therefore they are used for adjusting the colour of the composition, but not hair.

Additionally, the coloring compositions of the present invention can comprise neutral dyes (HC dyes), so called nitro dyes either alone or in addition to the cationic direct dyes.

Some examples to those are: HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Dyes in addition to the oil soluble dye can be included into the compositions of the present invention at a concentration of 0.0001 to 1%, preferably 0.0001 to 0.75% and more preferably 0.0001 to 0.5% by weight, calculated to total aqueous composition.

Hair cleansing colour enhancing compositions of the present invention can be in the form of conventional liquid thickened shampoo, as well in the form of ready to use foam, delivered either from a pump-foamer or from an aerosol bottle. In the case that an aerosol foam preparation is preferred, propellant gas must be added to the formulation. The suitable propellant gasses are carbon dioxide, dimethylether and alkanes such as butane propane or their mixtures.

The composition of the present invention comprises hair-conditioning agents. Conditioning agents can be selected from oily substances, non-ionic substances, cationic amphiphilic ingredients, cationic polymers or their mixtures.

Oily substances are selected from such as silicone oils, either volatile or non-volatile, natural and synthetic oils. Among silicone oils those can be added to the compositions include dimethicone, dimethiconol, polydimethylsiloxane, DC fluid ranges from Dow Corning, natural oils such as olive oil, almond oil, avocado oil, weizenkeim oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula

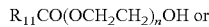
$R_{11}CO(OCH_2CH_2)_nOH$ or

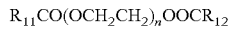
$R_{11}CO(OCH_2CH_2)_nOOCR_{12}$ where $R_{11}$ and $R_{12}$ are independent from each other saturated, unsaturated or branched or non-branched alkyl chain with 7 to 21 C atoms and n is typically 2-100.

In one of the preferred from of the present invention, coloring enhancing cleansing compositions comprise at least one cationic polymer as conditioning agent. Suitable cationic polymers are those of best known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-81, Quaternium-81, Quaternium-82, Quaternium-83 and Quaternium-84.

It has further been found out that especially those of cationic cellulose type polymers known as Polymer JR type from Amerchol such as Polyquaternium 10 or cationic guar gum known with trade name Jaguar from Rhône-Poulenc and chemically for example Guar hydroxypropyl trimonium chloride, are preferred ones. Furthermore, chitosan and chitin can also be included in the compositions as cationic natural polymers. In this context reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The most preferred cationic polymers are those of cationic cellulose derivatives, cationic guar gum derivatives, polyquaternium 6 and polyquaternium 7.

The cationic polymers also include the quaternized products of graft polymers from organopolysiloxanes and polyethyl oxazolines described in EP-A 524 612 and EP-A 640 643.

The compositions according to the invention may also comprise further conditioning substances such as protein hydrolyzates and polypeptides, e.g., keratin hydrolyzates, collagen hydrolyzates of the type "NutrilanR" or elastin hydrolyzates, as well as also in particular plant protein hydrolyzates, optionally, cationized protein hydrolyzates, e.g., "GluadinR".

Typical concentration range for any of those conditioners of cationic polymers, silicon oil and derivatives and cationic surfactants can be 0.01-5% by weight, preferably 0.01-3.5% by weight, more preferably 0.05-2.5% and most preferably 0.1-1.5% by weight calculated to the total composition.

Further conditioning additives are hair conditioning and/or styling polymers. These may be nonionic polymers, preferably alcohol- and/or water-soluble vinyl pyrrolidone polymers, such as a vinyl pyrrolidone homopolymers or copolymers, in particular with vinyl acetate. Useful vinyl pyrrolidone polymers are, e.g., those known by the trade name "Luviskol®", for example, the homopolymers "Luviskol® K 30, K 60 and K 90", as well as the water- or alcohol-soluble copolymers from vinyl pyrrolidone and vinyl acetate, distributed by BASF AG under the trade name "Luviskol® VA 55 respectively VA 64". Further possible nonionic polymers are vinyl pyrrolidone/vinyl acetate/vinyl propionate copolymers such as "Luviskol® VAP 343", vinyl pyrrolidone/(meth)acrylic acid ester copolymers, as well as chitosan derivatives.

Amphoteric polymers are found to be useful in conditioning shampoo composition of the present invention. They are incorporated alone or in admixture with at least one additional cationic, nonionic or anionic polymer, particularly copolymers of N-octyl acrylamide, (meth)acrylic acid and tert.-butyl aminoethyl methacrylate of the type "Amphomer®"; copolymers from methacryl oylethyl betaine and alkyl meth-acrylates of the type "Yukaformer®", e.g., the butyl methacrylate copolymer "Yukaformer® Am75"; copolymers from monomers containing carboxyl groups and sulfonic groups, e.g., (meth)acrylic acid and itaconic acid, with monomers such as mono- or dialkyl amino alkyl(meth) acrylates or mono- or dialkyl-aminoalkyl (meth)acrylamides containing basic groups, in particular amino groups; copolymers from N-octyl acrylamide, methyl methacrylate, hydroxypropyl methacrylate, N-tert.-butyl aminoethyl methacrylate and acrylic acid, as well as the copolymers known from U.S. Pat. No. 3,927,199, are applicable.

hydroxycarboxylic acid and/or dicarboxylic acid, show optimum performance in colour enhancing and especially surprisingly excellently superior performance in hair shine improving, excellently improving hair manageability and softness of hair. The compositions of the present invention improve also combability, volume and body of hair. After washing hair with the compositions of present invention, hair feels nicer when touching. The effects mentioned are more pronounced on repeated usage.

The pH of the compositions according to the present invention is suitably between 2 and 7 and preferably in the range of 2.5 to 6.0, more preferably 3 to 5.5 and most preferably 4 to 5.5.

The pH of the compositions is adjusted with hydroxycarboxylic acids and/or dicarboxylic acids. In those cases where selected hydroxycarboxylic acid and/or dicarboxylic acid concentration is not enough to reach the selected pH, other organic and inorganic acids can as well be used to adjust pH to the required value. The hydroxycarboxilic acids useful in the compositions of the present invention are lactic acid, glycolic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid.

Cleansing color enhancing composition of the present invention can be transparent as well as pearly. Transparency of the composition is judged by naked eye in a transparent shampoo bottle with a thickness not more than 5 cm. In the case a transparent appearance is wished, the following ingredients are not essential. However, pearl-shiny appearance is achieved with those dispersed in cleansing color enhancing compositions in crystalline form, i.e. so called pearl-shine or pearlizing agents. The preferred once are PEG-3 distearate and ethylene glycol distearate. The concentration of those can typically be from 0.1 to 3%, preferably 0.5 to 2% by weight, calculated to the total composition. These compounds are preferably added to the compositions in admixture with anionic, nonionic and/or amphoteric surfactants. Such kind of mixtures is available commercially.

Compositions of the present invention may comprise organic solvents such as ethanol, propanol, isopropanol, benzyl alcohol, benzyloxyethanol, ethoxydiglycol, alkylene carbonates such as ethylene carbonate and propylene carbonate, phenoxyethanol, butanol, isobutanol, cyclohexane, cyclohexanol, hexyleneglycol, ethylenecarbonate, propyleneglycol, ethyleneglycol monoethylether, ethylene glycol monobutyl ether, ethylene glycol monophenyl ether, 1-phenylethylalcohol, 2-phenylethylalcohol, o-methoxyphenol. The most preferred ones are benzyloxyethanol and polypropylene glycols. Concentration of organic solvents in the shampoo composition should not exceed 5% by weight, preferably in the range of 0.1 to 3%, more preferably 0.5 to 2.5% by weight calculated to total composition.

Solubilizers may be added to the compositions especially when oily substances are chosen as conditioning agents and fragrance oils with highly lipophilic properties. Typical solubilizers may be hydrogenated castor oil known with the trade mark Cremophor RH series from BASF. It should be noted that as well the surfactant mixture can be a good solubilizer for fragrance oils. Typical concentration of the solubilizers can be in the range of 0.01-2% by weight, preferably 0.1-1% by weight, calculated to total composition.

The coloring shampoo composition may contain active ingredients selected from UV filters, moisturisers, sequestering agents, and natural ingredients.

The moisturizing agents are selected from panthenol, polyols, such as glycerol, polyethylene glycols with molecular weight 200 to 20,000. The moisturizing ingredients can be included in the conditioner compositions at a concentration range of 0.01-2.5% by weight calculated to the total composition.

The sequestering agents are selected from polycarboxy acids. The preferred one is ethylene diamine tetraacetic acid, EDTA. Typical useful concentration range for sequestering agents is of 0.01-2.5% by weight calculated to the total composition.

The UV filters are that oil and water soluble ones for the purpose of protecting hair colour. In other words, anionic and nonionic, oily, UV filters are suitably used in the compositions of the present invention. Suitable UV-absorbing substances is are: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzylidenecampher, 3-(4'-sulfo)-benzyl-idenebornane-2-one and the salts thereof and/or 3-(4'-methyl benzylidene)-DL-campher. The amount of the UV-absorber ranges typically from about 0.01% to 2.5%, more preferably from 0.05% to 1% by weight, calculated to the total composition.

Natural plant extracts are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, the various "Extrapon®" products, "HerbasolR", "SedaplantR" and "HexaplantR". Extracts and the preparation thereof are also described in "Hagers Handbuch der pharmazeutischen Praxis", 4th Ed.

The viscosity of the conditioning shampoo compositions according to the invention is in the range of 500 and about 20,000 mPa·s at 20° C., preferably 1,000 to 10,000, in particular 1,000 to 7,000 mPa·s at 20° C., measured with Brookfield or Höppler viscosimeters at a shear rate of 10 sec−1. Viscosity of shampoo compositions can be adjusted with known viscosity enhancers. The preferred ones are PEG-55 propyleneglycol oleate and PEG-18 glyceryl oleate/cocoate known with the trade names AntilR 141 and 171, respectively and PEG-160 sorbitan triisostearate known with a trade name RheodolR. It should be noted that in the case that a composition are delivered in the form of a foam from a pump-foamer and/or aerosol can, those compositions should not be thickened and have a viscosity value not more than 500 mPa·s, more preferably 250 mPa·s measured as mentioned above at room temperature.

It is self-understood that the shampoos according to the invention may comprise other substances customarily used in such compositions such as preservatives, fragrances. A list of such additives can also be found in Schrader, I.c., on pp. 695 to 722.

It should especially be noted that the effects of the inventive compositions become more and more visible after repeated usage. Especially colour and shine enhancing effect is very much pronounced after repeated usage.

The following examples are to illustrate the invention, but not to limit.

EXAMPLE 1

| | |
|---|---|
| Sodium lauryl ether carboxylate (10EO) | 5.0 (% by wt.) |
| C8-C22-Alkyl glucoside (P.D.: ~1.5) | 5.0 |
| Cocoamidopropyl betaine | 5.0 |
| Cetyl PEG/PPG-10/1 dimethicone | 0.5 |
| Cationic polymer (Polyquaternium-6) | 0.1 |
| PEG-18 Glyceryl cocoate/oleate | 1.0 |
| Cl 60725 | 0.075 |
| Dipropylene glycol | 1.0 |
| Cetrimonium chloride | 1.0 |
| Malic acid | q.s. to pH 5.2 |
| Perfume, preservative | q.s. |
| Water | q.s. to 100.0 |

Above composition was prepared in the following way: the dyestuff CI 60725 was dissolved in dipropylene glycol and cetrimonium chloride was mixed into the solution. In a separate vessel all surfactants were combined and cationic polymer as an aqueous solution and silicone compound was mixed into the surfactant mix. Subsequently the mixture of dye, dipropyleneglycol and cationic surfactant was added. Finally the thickener PEG-18 Glyceryl cocoate/oleate, fragrance and preservative was added and pH was adjusted.

The above composition showed excellent anti yellow effect on gray and bleached hair. The hair washed with the above composition felt excellently clean, soft and smooth both in wet and dry stages and especially shiny and soft in dry stage. Stylability and manageability was improved as well.

EXAMPLE 2

| | |
|---|---|
| C12-C14-alkyl glucoside (P.D.: ~1.4) | 8.0 |
| Cocoamidopropyl betaine | 5.0 |
| Sodium laureth sulfate | 1.0 |
| Sodium lauroyl glutamate | 4.0 |
| PEG-3 distearate | 0.8 |
| PEG-18 Glyceryl cocoate/oleate | 1.0 |
| Cl 60725 | 0.075 |
| Dipropylene glycol | 1.0 |
| Quaternium-80 | 1.0 |
| Lactic acid | q.s. to pH 5.0 |
| Perfume, preservative | q.s. |
| Water | ad100.0 |

Above composition was prepared in the same way as in example 1 and showed similar effects on hair.

EXAMPLE 3

| | |
|---|---|
| C12-C14-alkyl glucoside (P.D.: ~1.4) | 7.0 |
| Cocoamidopropyl betaine | 6.0 |
| Sodium laureth sulfate | 1.0 |
| Sodium lauroyl glutamate | 5.0 |
| Polyqauternium-6 | 0.4 |
| PEG-18 Glyceryl cocoate/oleate | 1.0 |
| Cl 60725 | 0.075 |
| Basic red 51 | 0.02 |
| Dipropylene glycol | 1.0 |
| Quaternium-80 | 1.0 |
| Lactic acid | q.s. to pH 5.5 |
| Perfume, preservative | q.s. |
| Water | ad100.0 |

Above composition was prepared in the same way as in example 1 except that Basic red 51 was dissolved in a small portion of water and mixed directly to the surfactant mix. Here again it was observed that bleached hair feels soft and smooth, easily combable and has shiny blonde appearance with much less yellowish appearance. Upon repeated usage, the above effects were more pronounced.

EXAMPLE 4

| | |
|---|---|
| C12-C14-alkyl glucoside (P.D.: ~1.4) | 3.0 |
| Laureth-22 | 3.0 |
| Cocoamidopropyl betaine | 6.0 |
| Sodium lauroyl glutamate | 6.0 |
| Polyqauternium-10 | 0.5 |
| PEG-18 Glyceryl cocoate/oleate | 1.0 |
| Cl 60725 | 0.09 |
| Acid red 51 | 0.03 |
| Dipropylene glycol | 1.0 |
| Cetrimonium chloride | 1.0 |
| Citric acid | q.s. to pH 5.5 |
| Perfume, preservative | q.s. |
| Water | ad100.0 |

Above composition was prepared in the same way as in example 1 except that Acid red 52 was dissolved in a small portion of water and mixed directly to the surfactant mix. Here again it was observed that gray hair feels soft and smooth, easily combable and has shiny silver gray appearance with much less yellow colour. Upon repeated usage, the above effects were more pronounced.

EXAMPLE 5

| | |
|---|---|
| C12-C14-alkyl glucoside (P.D.: ~1.4) | 3.0 |
| Laureth-22 | 3.0 |
| Cocoamidopropyl betaine | 6.0 |
| Sodium lauroyl glutamate | 6.0 |
| Polyqauternium-10 | 0.5 |
| PEG-18 Glyceryl cocoate/oleate | 1.0 |
| Benzophenone-3 | 0.2 |
| Cl 60725 | 0.09 |
| Basic red 51 | 0.03 |
| Dipropylene glycol | 1.0 |
| Quaternium-80 | 1.0 |
| Citric acid | q.s. to pH 5.5 |
| Perfume, preservative | q.s. |
| Water | ad100.0 |

Above composition was prepared in the same way as in example 1 except that Basic red 52 was dissolved in a small portion of water and mixed directly to the surfactant mix. Here again it was observed that gray hair feels soft and smooth, easily combable and has shiny silver gray appearance with much less yellow colour. Upon repeated usage, the above effects were more pronounced.

EXAMPLE 6

| | |
|---|---|
| C12-C14-alkyl glucoside (P.D.: ~1.4) | 5.0 |
| Cocoamidopropyl betaine | 6.0 |
| Sodium lauroyl glutamate | 6.0 |
| Polyqauternium-10 | 0.5 |
| PEG-18 Glyceryl cocoate/oleate | 1.0 |
| Benzophenone-3 | 0.3 |
| Cl 60725 | 0.1 |
| HC Red 3 | 0.02 |
| Dipropylene glycol | 1.0 |
| Cetrimonium chloride | 1.0 |
| Citric acid | q.s. to pH 5.5 |
| Perfume, preservative | q.s. |
| Water | ad 100.0 |

Above composition was prepared in the same way as in example 1 except that HC red 3 was dissolved in a small portion of water and mixed directly to the surfactant mix. Here again it was observed that bleached hair feels soft and smooth, easily combable and has shiny appearance with much less yellow colour. Upon repeated usage, the above effects were more pronounced.

EXAMPLE 7

| | |
|---|---|
| C12-C14-alkyl glucoside (P.D.: ~1.4) | 5.0 |
| Cocoamidopropyl betaine | 6.0 |
| Sodium lauroyl glutamate | 6.0 |
| Polyqauternium-10 | 0.5 |
| PEG-18 Glyceryl cocoate/oleate | 1.0 |
| Benzophenone-3 | 0.3 |
| Cl 60725 | 0.09 |
| Basic red 51 | 0.03 |
| PPG-3 | 1.0 |
| Cocamidoproplyethyldimonium methosulfate | 1.0 |
| Citric acid | q.s. to pH 5.5 |
| Perfume, preservative | q.s. |
| Water | ad 100.0 |

Above composition was prepared in the same way as in example 1 except that Basic red 52 was dissolved in a small portion of water and mixed directly to the surfactant mix. Here again it was observed that gray hair feels soft and smooth, easily combable and has shiny silver gray appearance with much less yellow colour. Upon repeated usage, the above effects were more pronounced.

The invention claimed is:

1. A coloring enhancing shampoo composition for hair comprising at least one cleansing and lathering surfactant selected from anionic, nonionic and amphoteric surfactants and present at a concentration of 5 to 50% by weight, calculated to total composition; at least one oil soluble dye; at least one polypropylene glycol compound according to the formula $$H(OCH_2CH)_nOH$$
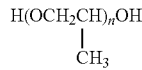

wherein n is a number in the range of 2 to 50; and at least one cationic surfactant of the following general formula

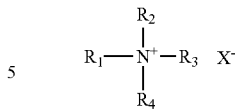

wherein $R_1$ is an saturated or unsaturated alkyl chain with 12 to 22 C atoms, or

where $R_5$ is saturated or unsaturated, alkyl chain with 7-21 C atoms and n has value of 1-4, or

where $R_6$ is saturated or unsaturated, branched or non-branched alkyl chain with 7-21 C atoms and n has value of 1-4, and R2, R3 and R4 are same or different and independent from each other an alkyl group with 1 to 4 C atoms, and X is an anion such as chloride, bromide, methosulfate; and optionally comprising at least one silicone compound having at least one quaternary ammonium group.

2. The composition according to claim 1 wherein the oil soluble dyes are selected from CI 12100, CI 12140, CI 12700, CI 12740, CI 26100, CI 26105, CI 45396, CI 45410, CI 45425, CI 47000, CI 60725, CI 60724, CI 61520 and CI 61565.

3. The composition according to claim 1 wherein the polypropylene glycol is selected from dipropylene glycol, PPG-3, PPG-9, PPG-12, PPG 15, PPG-16, PPG 20 and is present at a concentration of 0.1 to 10% by weight, calculated to total composition.

4. The composition according to claim 1 comprising mono alkyl quaternary ammonium surfactant at a concentration of 0.1 to 3% by weight calculated to total composition.

5. The composition according to claim 4 wherein the mono alkyl quaternary ammonium surfactant is cetrimonium chloride.

6. The composition according to claim 4 wherein the silicone compound with at least one quaternary ammonium group is Quaternium-80.

7. The composition according to claim 1 comprising at least one non-ionic surfactant.

8. The composition according to claim 1 comprising at least one amphoteric surfactant.

9. The composition according to claim 1 comprising at least one anionic carboxylate surfactant.

10. The composition according to claim 1 comprising at least one additional direct dye selected from anionic, cationic and non-ionic nitro dye.

11. The composition according to claim 10 comprising at least one cationic direct dye at a concentration of 0.0001 to 1% by weight, calculated to total composition.

12. The composition according to claim 1 further comprising conditioning agents selected from oily substances, non-ionic substances, cationic polymers or mixtures thereof.

13. The composition according to claim 1 further comprising at least one UV filter.

14. A method of cleansing and colour enhancing hair wherein a composition according to claim 1 is applied to wet hair; foamed by massaging; and rinsed of after a processing time with water.

15. A method of producing cleansing and colour enhancing composition according to claim 1 wherein oil soluble dye is dissolved in at least one polypropylene glycol and mixed with at least one cationic surfactant and/or silicone compound with at least one quaternary ammonium group and subsequently added to a surfactant/water mixture which is furthermore added the remaining ingredients in the formulation.

16. The composition according to claim 1 comprising at least one silicone compound having at least one quaternary ammonium group present at concentration of 0.1 to 3% by weight calculated to total composition.

* * * * *